US009316596B2

(12) United States Patent
Lévesque (10) Patent No.: US 9,316,596 B2
(45) Date of Patent: Apr. 19, 2016

(54) APPARATUS AND METHOD FOR INSPECTING MATTER AND USE THEREOF FOR SORTING RECYCLABLE MATTER (75) Inventor: Marc Lévesque, St-Augustin-de-Desmaures (CA)

(73) Assignee: INDUSTRIES MACHINEX INC., Plessisville (CA)

(*) Notice: Subject to any disclaimer, the term of this patent is extended or adjusted under 35 U.S.C. 154(b) by 31 days.

(21) Appl. No.: 14/236,265

(22) PCT Filed: Aug. 19, 2011

(86) PCT No.: PCT/IB2011/053664
§ 371 (c)(1),
(2), (4) Date: Jan. 30, 2014

(87) PCT Pub. No.: WO2013/027083
PCT Pub. Date: Feb. 28, 2013

(65) Prior Publication Data
US 2014/0160472 A1 Jun. 12, 2014

(51) Int. Cl.
G01N 21/55 (2014.01)
G01N 21/90 (2006.01)
G01B 11/24 (2006.01)
G01N 21/88 (2006.01)
B07C 5/342 (2006.01)
G01N 21/84 (2006.01)

(52) U.S. Cl.
CPC ............... *G01N 21/88* (2013.01); *B07C 5/342* (2013.01); *G01N 21/55* (2013.01); *G01N 21/90* (2013.01); *G01B 11/24* (2013.01); *G01N 2021/845* (2013.01); *G05B 2219/37572* (2013.01); *G05B 2219/45047* (2013.01)

(58) Field of Classification Search
CPC .......... B07C 5/342; G01N 21/55; G01B 11/24
USPC .............. 356/237.1–241.6, 242.1–243.8, 356/426–431, 600–640
See application file for complete search history.

(56) References Cited

U.S. PATENT DOCUMENTS 3,325,649 A * 6/1967 Bird ......................... 250/559.01
3,747,755 A * 7/1973 Senturia .................. B07C 5/342
209/559

(Continued)

FOREIGN PATENT DOCUMENTS

CA 1219933 3/1987
WO 96/06689 A2 3/1996

(Continued)

*Primary Examiner* — Kara E Geisel
*Assistant Examiner* — Jarreas C Underwood
(74) *Attorney, Agent, or Firm* — Fasken Martineau DuMoulin LLP (57) ABSTRACT An apparatus and a method for inspecting matter and the use thereof for sorting recyclable material including transparent material are disclosed. The apparatus comprises a lighting unit for projecting a concentrated diffused lighting onto the matter to generate a specular reflected light beam representative of the inspected matter. The apparatus comprises an imaging unit mounted according to a given imaging angle with respect to the projected concentrated diffused lighting for imaging the specular reflected light beam to provide image data representative of the inspected matter. The apparatus comprises an analyzing unit for analyzing the image data and providing matter characterization data based on the specular reflected light beam representative of the inspected matter.

21 Claims, 7 Drawing Sheets

(56) References Cited

U.S. PATENT DOCUMENTS

| | | | |
|---|---|---|---|
| 4,767,911 A * | 8/1988 | Maram et al. | 219/130.01 |
| 4,918,517 A * | 4/1990 | Burgoon | 348/90 |
| 5,477,332 A * | 12/1995 | Stone | G01N 21/55 348/128 |
| 5,481,085 A * | 1/1996 | Kovacevic | B23K 9/1274 219/130.01 |
| 5,991,038 A * | 11/1999 | Yamamoto | G01B 11/306 356/237.2 |
| 6,353,197 B1 | 3/2002 | Ulrichsen et al. | |
| 6,760,116 B2 * | 7/2004 | Iwasaki | G01B 11/24 356/3.01 |
| 7,115,869 B2 * | 10/2006 | Shelley et al. | 250/341.8 |
| 7,262,380 B1 | 8/2007 | Ulrichsen et al. | |
| 8,131,192 B2 * | 3/2012 | Honguh | B41J 29/393 399/289 |
| 8,437,002 B2 * | 5/2013 | Horvath | G01B 11/0625 356/237.1 |
| 2001/0021023 A1 * | 9/2001 | Ishikawa | G02B 27/021 356/445 |
| 2002/0141006 A1 | 10/2002 | Pocius et al. | |
| 2003/0151746 A1 | 8/2003 | Sperling et al. | |
| 2004/0095571 A1 | 5/2004 | Bourely et al. | |
| 2006/0102528 A1 | 5/2006 | Bourely | |
| 2006/0256341 A1 | 11/2006 | Kuwada | |
| 2008/0246969 A1 * | 10/2008 | Imura | G01N 21/57 356/445 |
| 2009/0032445 A1 | 2/2009 | Doak et al. | |
| 2010/0091272 A1 | 4/2010 | Asada et al. | |
| 2010/0290032 A1 * | 11/2010 | Bugge | 356/51 |
| 2011/0181873 A1 | 7/2011 | Yavets-Chen et al. | |

FOREIGN PATENT DOCUMENTS

| | | |
|---|---|---|
| WO | 99/20048 A1 | 4/1999 |
| WO | 00/57160 A2 | 9/2000 |
| WO | 02/074457 A1 | 9/2002 |
| WO | 2004/016362 A1 | 2/2004 |
| WO | 2005/106438 A1 | 11/2005 |

* cited by examiner

APPARATUS AND METHOD FOR INSPECTING MATTER AND USE THEREOF FOR SORTING RECYCLABLE MATTER

CROSS-REFERENCE TO RELATED APPLICATIONS

The present application is a national phase entry of PCT Application No. PCT/IB2011/053664, entitled "APPARATUS AND METHOD FOR INSPECTING MATTER AND USE THEREOF FOR SORTING RECYCLABLE MATTER" filed on Aug. 19, 2011, the specification of which is hereby incorporated by reference.

FIELD OF THE INVENTION

The invention relates to an apparatus and a method for inspecting matter using specular reflected light. It also relates to applications of the method for performing automatic material sorting, automatic classification of transparent material and automatic process control as non-limitative examples.

BACKGROUND OF THE INVENTION

Figure 1:
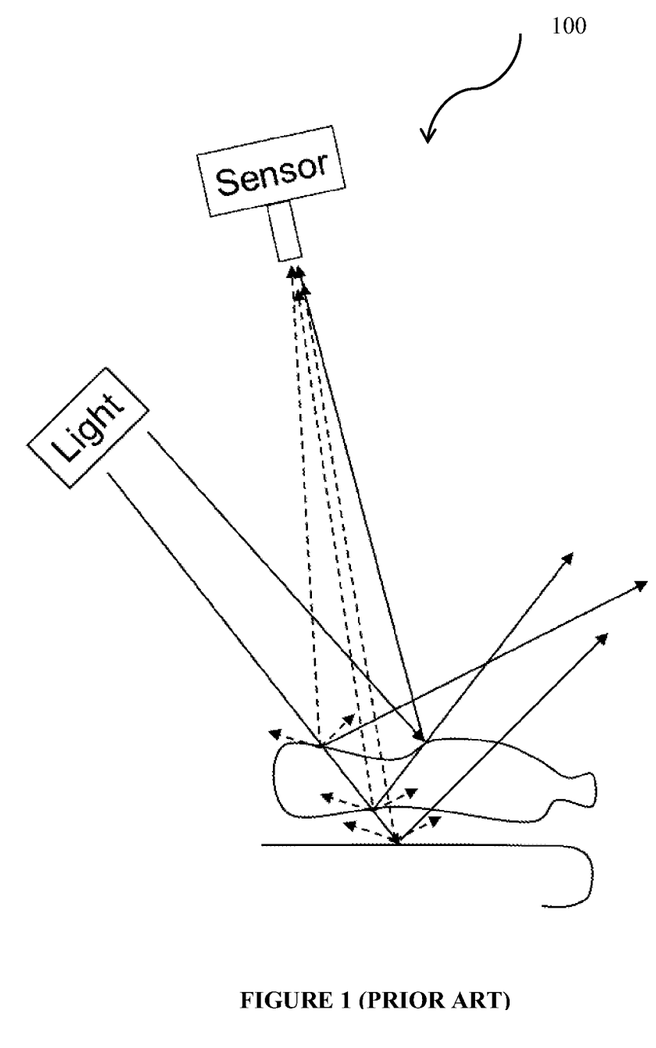
FIG. 1 (PRIOR ART) shows a schematic representation of a typical configuration of an apparatus for inspecting matter enabling to minimize specular reflected rays reaching the imaging unit.

Imaging systems for obtaining spectral data of a plurality of inspection points of an inspected surface are widely used for automatically inspecting various objects in a great variety of applications such as automated recycling of plastic and other materials for example. They generally comprise a lighting unit for projecting light onto the objects conveyed and an imaging unit for imaging the light reflected from the objects, as illustrated in the imaging system 100 of FIG. 1 (PRIOR ART). The reflected light may then be analyzed to characterize the objects before sorting them.

Such imaging systems devised to automatic material sorting are described in U.S. Pat. No. 7,113,272 and in PCT application publication numbers WO2004016362; WO9606689; WO0057160 and WO2005106438.

Each of these references discloses an imaging system minimizing or eliminating specular reflections which are described as parasite reflections. They rely on diffused reflected light to characterize the objects.

Although these systems may be generally suitable for inspection of objects having diffusing surfaces, they may not be adapted for inspecting transparent and/or light material having poorly diffusing surfaces, which is of great disadvantage.

Indeed, in the prior art systems, a small quantity of diffused light is nevertheless reflected by the poorly diffusing surfaces but the measured signal is generally too small to provide accurate information. Moreover, the measured signal may even be lost in the noise in some cases.

In order to overcome this disadvantage, it has been proposed to rely on diffused light reflected by a surface located under the transparent object and which has traveled through the object under inspection.

In the case of automatic material sorting, a conveying belt is used for conveying the objects under the imaging system and then to a sorting station. The diffused light reflected by the belt may then be used. However, in many applications, nominal conditions of the belt may change over time and prevent a reliable inspection of the objects, which is of great disadvantage.

For example, in the case the belt is clean, his surface may be highly specular, thereby preventing diffused reflections towards the imaging unit. Alternatively, in the case the belt is dirty, diffused reflections towards the imaging unit may be enabled, but these reflections may not be considered as enough reliable for some applications since they may be altered by the spectral signature of the conveying belt.

Moreover, even if the proposed configurations help minimizing the specular reflections, such specular reflections may nevertheless reach the imaging unit and saturate the imaging element. In order to reduce this issue, the imaging element may be provided with a high dynamic range in order to minimize saturation issues while enabling maximum detection of diffused light, but saturation issues may still arise.

Other configurations wherein each of the imaging unit and the lighting unit extends on both side of the matter respectively have been proposed for imaging light passing through transparent objects, but they may not be conveniently and cost-effectively implemented in an online industrial process, particularly in dirty environments, which is of great disadvantage.

It would therefore be desirable to provide an improved apparatus and an improved method for inspecting various objects that would reduce at least one of the abovementioned drawbacks.

BRIEF SUMMARY

Accordingly, there is provided an apparatus for inspecting matter, the apparatus comprising a lighting unit for projecting a concentrated diffused lighting onto at least a portion of the matter to generate a specular reflected light beam representative of the inspected matter. The apparatus comprises an imaging unit mounted according to a given imaging angle with respect to the projected concentrated diffused lighting for imaging at least a portion of the specular reflected light beam to provide image data representative of the inspected matter. The apparatus also comprises an analyzing unit operatively connected to the imaging unit for analyzing the image data and providing matter characterization data based on the at least a portion of the specular reflected light beam representative of the inspected matter.

The apparatus may enable a reliable inspection of transparent and light material without relying on a conveying surface on which objects lie, which is of great advantage since the optical properties of the conveying surface may change or become non-uniform over time.

The apparatus may also enable automatic material sorting and automatic classification of transparent material, which is of great advantage.

Moreover, the apparatus may be adapted for online industrial process wherein the matter is provided in a continuous flow, which is also of great advantage.

Moreover, the apparatus may be simple to implement and maintain and does not need time consuming calibration or fine tuning procedures, which is of great advantage for cost-effectively inspecting matter.

In one embodiment, the concentrated diffused lighting is angularly projected onto the matter.

In one embodiment, the specular reflected light beam comprises a plurality of specular rays selected from a group consisting of specular rays of second surface, specular rays of third surface and specular rays of fourth surface.

In a further embodiment, the specular reflected light beam further comprises specular rays of a supporting surface supporting the matter.

In one embodiment, the concentrated diffused lighting further generates a diffused reflected light beam representative of the inspected matter and the imaging unit is adapted for imaging at least a portion of the diffused reflected light beam.

In a further embodiment, the matter characterization data are further based on the at least a portion of the diffused reflected light beam.

This is of great advantage since it may enable a reliable inspection of differing materials such as a flow of matter comprising opaque materials and transparent materials.

In one embodiment, the matter characterization data comprises matter identification data. This may be of great advantage for plastic classification applications.

In one embodiment, the projected concentrated diffused lighting and the imaging unit extend at a similar angle on each side of a normal of a surface of the matter. This may be of great advantage for maximizing specular reflections generated by horizontal surfaces.

In another embodiment, the projected concentrated diffused lighting and the imaging unit extend on a side of a normal of a supporting surface supporting the matter. This may be of great advantage for minimizing specular reflections generated by horizontal surfaces while increasing specular reflections generated by non-horizontal surfaces.

In one embodiment, the lighting unit comprises a converging lens and a limited diffusion angle diffuser mounted with a light source, the converging lens being mounted proximal the light source. In a further embodiment, the converging lens and the limited diffusion angle diffuser are integrated in a Fresnel lens.

In another embodiment, the lighting unit comprises a limited diffusion angle reflector mounted with a light source. In a further embodiment, the limited diffusion angle reflector comprises a patterned aluminum sheet providing a diffusing mirror.

In yet another embodiment, the lighting unit comprises a diffuser and a converging optical element mounted with a light source, the diffuser being mounted proximal the light source. In a further embodiment, the converging optical element comprises a converging mirror.

In still a further embodiment, the apparatus comprises a control unit operatively connected to the lighting unit for controlling projection of the concentrated diffused lighting and thereby relative intensities of the specular reflected light beam and the diffused reflected light beam. In one embodiment, the solid angle of the projected concentrated diffused lighting may be adjusted according to a given application.

In one embodiment, the projected concentrated diffused lighting has a given intensity enabling generation of the specular reflected light beam with an intensity adapted to a dynamic range of the imaging unit.

In one embodiment, the projected concentrated diffused lighting has a solid angle comprised between 0.15 steradian and 0.6 steradian, and the apparatus further comprises a control unit operatively connected to the lighting unit for controlling the solid angle of the concentrated diffused lighting.

In one embodiment, the matter comprises transparent material.

In one embodiment, the matter comprises waste of differing materials.

According to another aspect, there is also provided a method for inspecting matter, the method comprising projecting a concentrated diffused lighting onto at least a portion of the matter for generating a specular reflected light beam representative of the inspected matter; imaging at least a portion of the specular reflected light beam to provide image data representative of the inspected matter; and analyzing the image data for providing matter characterization data based on the at least a portion of the specular reflected light beam representative of the inspected matter.

In one embodiment, the processing step of projecting a concentrated diffused lighting onto at least a portion of the matter comprises providing a lighting beam; concentrating the lighting beam to provide a concentrated lighting; and diffusing the concentrated lighting according to a given limited diffusion angle to thereby provide the concentrated diffused lighting.

In another embodiment, the processing step of projecting a concentrated diffused lighting onto at least a portion of the matter comprises providing a lighting beam; and reflecting the lighting beam towards the at least a portion of the matter according to a given limited diffusion angle to thereby provide the concentrated diffused lighting.

In yet another embodiment, the processing step of projecting a concentrated diffused lighting onto at least a portion of the matter comprises providing a lighting beam; diffusing the lighting beam for providing a diffused lighting; and converging the diffused lighting towards the at least a portion of the matter to thereby provide the concentrated diffused lighting.

In still a further embodiment, the method further comprises projecting an additional concentrated diffused lighting onto the at least a portion of the matter for generating an additional specular reflected light beam representative of the inspected matter; and imaging at least a portion of the additional reflected light beam to provide additional image data representative of the inspected matter. This is of great advantage since it may enable to enhance image data for various relative orientations of the surface of the matter.

In one embodiment, the processing step of analyzing the image data comprises determining a spectral absorption of the inspected matter.

According to another aspect, there is also provided the use of the method for inspecting matter as defined above for automatic material sorting.

According to another aspect, there is also provided the use of the method for inspecting matter as defined above for automatic classification of transparent material.

According to another aspect, there is also provided the use of the method for inspecting matter as defined above for automatic manufacturing process control.

These and other objects, advantages and features of the present invention will become more apparent to those skilled in the art upon reading the details of the invention more fully set forth below.

BRIEF DESCRIPTION OF THE DRAWINGS

In order that the invention may be readily understood, embodiments of the invention are illustrated by way of example in the accompanying drawings.

Further details of the invention and its advantages will be apparent from the detailed description included below.

DETAILED DESCRIPTION

In the following description of the embodiments, references to the accompanying drawings are by way of illustration of examples by which the invention may be practiced. It will be understood that various other embodiments may be made and used without departing from the scope of the invention disclosed.

There is disclosed an apparatus and a method for inspecting matter which may be particularly well adapted for inspecting various transparent and/or light materials which are generally poorly diffusing, as a non-limitative example, while being also adapted for inspecting other types of material. As it will become more apparent to the skilled addressee throughout the reading of the present description, specular reflected light representative of the inspected matter is used to provide matter characterization data. In one embodiment, a spectral absorption of the inspected matter may be determined from the specular reflected light, as detailed below.

Throughout the present description, the apparatus for inspecting matter and the implementation of the related method will be mainly described according to a specific automatic material sorting application. The skilled addressee will nevertheless appreciate that the method may be used for various other applications, comprising automatic classification of transparent material and automatic process control as non-limitative examples.

Figure 4:
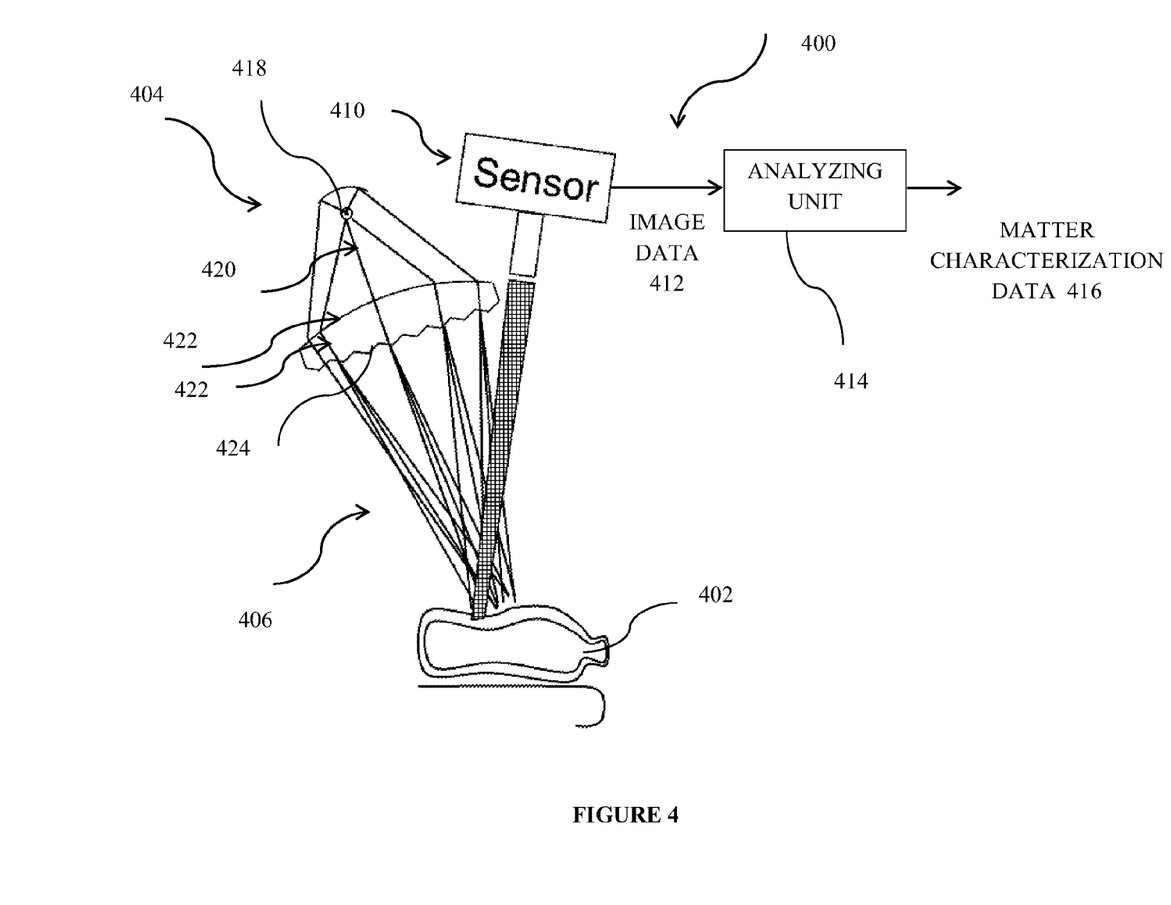
FIG. 4 shows an apparatus for inspecting matter, according to one embodiment.

Referring to FIG. 4, there is shown an apparatus 400 for inspecting matter 402 according to one embodiment. The apparatus 400 comprises a lighting unit 404 for projecting a concentrated diffused lighting 406 onto a portion of the matter 402 to generate a specular reflected light beam 408 representative of the inspected matter 402, as better shown in FIGS. 6A and 6B.

In one embodiment, the specular reflected light beam 408 comprises a plurality of specular rays selected from a group consisting of specular rays of second surface, specular rays of third surface and specular rays of fourth surface.

Figure 2:
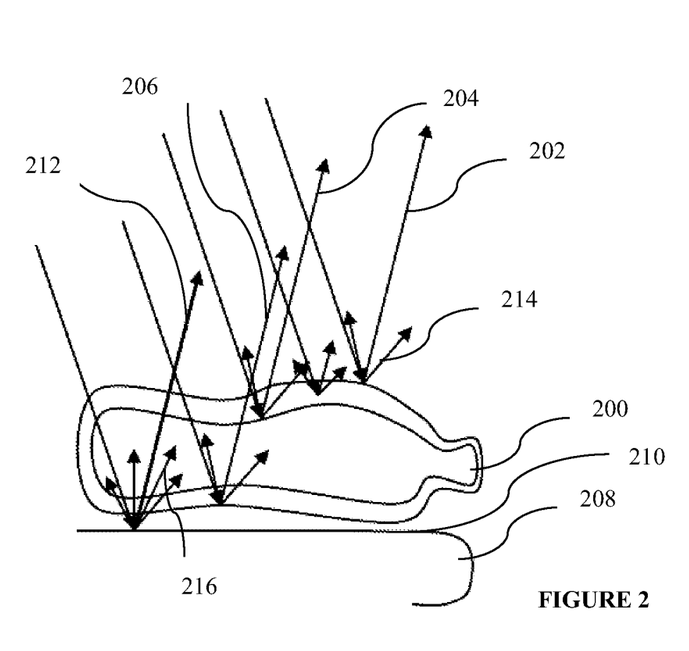
FIG. 2 illustrates various types of lighting rays reflected from an object under inspection, according to one embodiment.

Indeed, referring to FIG. 2 which shows various types of lighting rays reflected from a transparent bottle 200 under inspection, a specular ray of first surface 202 does not carry any useful information about the material since the ray does not penetrate it. Nevertheless, in some cases such as wherein the object under inspection is made of light or transparent material, a specular reflected ray of first surface 202 is generally accompanied with a specular reflected ray of second surface 204. Since this specular ray of second surface 204 penetrates through the material of the bottle 200, it carries a spectral signature representative of the material under inspection which may be analyzed to characterize the material.

FIG. 2 also shows a specular reflected ray of fourth surface 206 which may also be used. Indeed, since this specular reflected ray 206 travels two times through the wall of the object 200, it also carries a spectral signature representative of the material under inspection.

Figure 3:
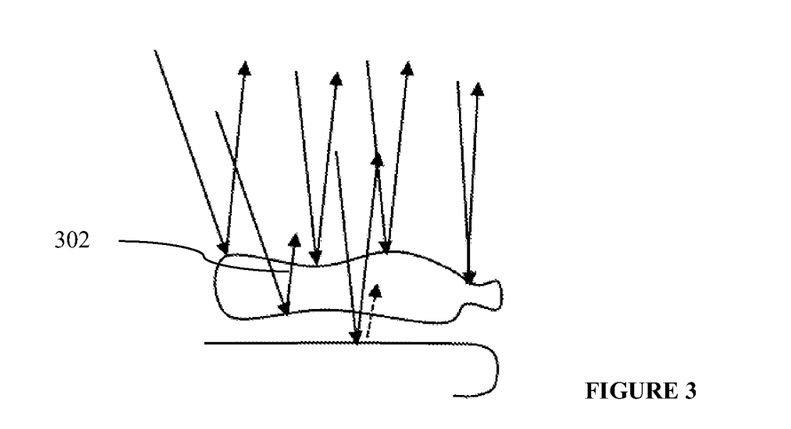
FIG. 3 shows a schematic representation of a projected lighting enabling maximizing specular reflected rays reaching an imaging unit, according to one embodiment.

In the case the object lies on a conveying belt 208 or any other support, the top surface 210 of the conveying belt 208 may act as a fifth surface for reflecting light received through the transparent material. As for the specular reflected rays of second surface 204, third surface 302 (shown in FIG. 3) and fourth surface 206, specular reflected rays of fifth surface 212 carry a spectral signature representative of the material of the bottle 200 and may also be reliably used.

As it will be more detailed below, diffuse reflections represented with short arrows and coming from the volume of the bottle 200 may be collected in a further embodiment since they are reliably representative of the material under inspection. As apparent to the skilled addressee, diffused reflected rays of first surface 214 do not carry any useful information about the material since the rays do not penetrate it.

It is also worth mentioning that diffused reflected rays of fifth surface 216, i.e. coming from the top surface 210 of the conveying belt 208 may also be useful under some circumstances. Indeed, such diffused reflected rays of fifth surface 216 may carry information relative to the material of the bottle 200 but it may also contain information relative to the conveying belt 208.

A smooth or scratched conveying belt may act as a reliable reflector for providing specular reflected rays of fifth surface 212.

The skilled addressee will appreciate that specular rays of first surface 202 may be comprised in the specular reflected light beam 408. However, the specular reflected light beam 408 may comprise enough useful specular reflected rays enabling a reliable analysis thereof, as detailed below.

Figures 7A, 7B, 8A, 8B:
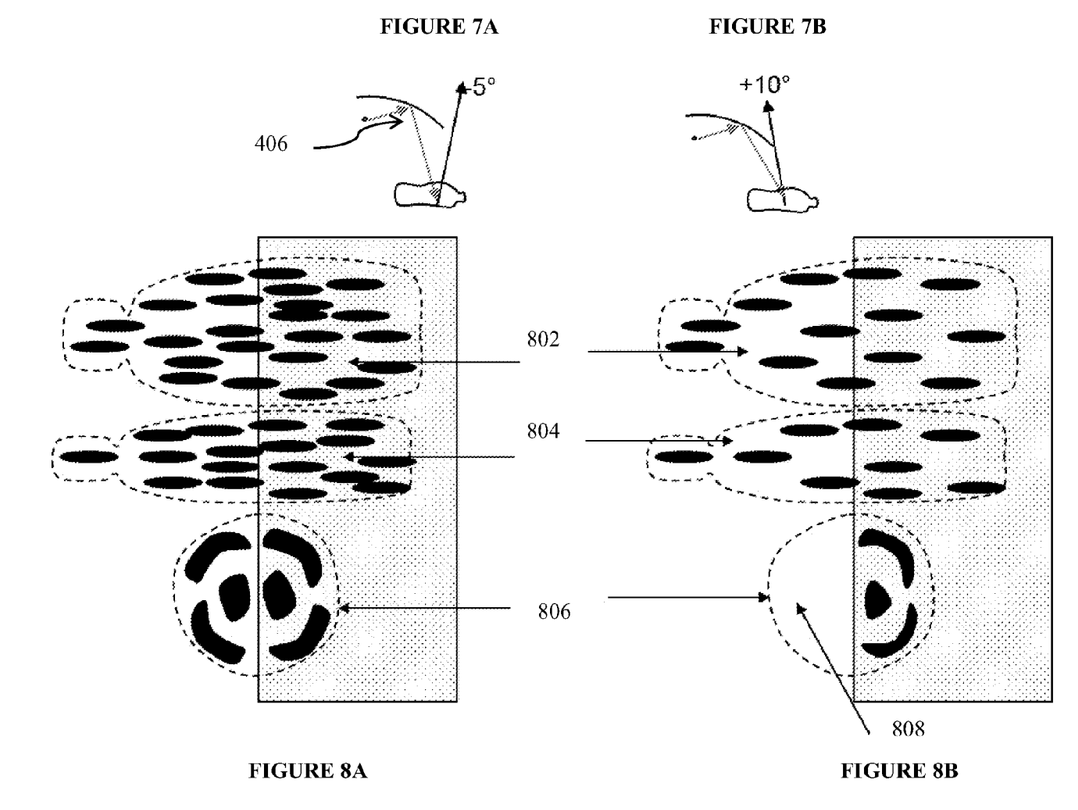
FIG. 7A shows a schematic representation of the relative angular positioning of the lighting unit and the imaging unit of an apparatus for inspecting matter, according to one embodiment.
FIG. 7B shows another schematic representation of the relative angular positioning of the lighting unit and the imaging unit of an apparatus for inspecting matter, according to another embodiment.
FIG. 8A shows image data obtained with an apparatus for inspecting matter mounted according to the configuration shown in FIG. 7A, according to one embodiment.
FIG. 8B shows image data obtained with an apparatus for inspecting matter mounted according to the configuration shown in FIG. 7B, according to one embodiment.

Referring again to FIG. 4, the apparatus 400 for inspecting matter 402 comprises an imaging unit 410 mounted according to a given imaging angle with respect to the projected concentrated diffused lighting 406. The imaging unit 410, which is a camera or a hyper-spectral camera in one embodiment, is adapted for collecting and imaging at least a portion of the specular reflected light beam 408 to provide image data 412 representative of the inspected matter 402, as shown in FIGS. 8A and 8B and described below. As detailed below, the given imaging angle may be chosen according to a particular application. For example, the given imaging angle may be chosen to maximize or minimize the specular reflected light coming from horizontal surfaces or other specifically oriented surfaces.

In the above described embodiment, the concentrated diffused lighting 406 is angularly projected onto the matter 402 but the skilled addressee will appreciate that other arrangements may be envisaged for a particular application.

The apparatus 400 for inspecting matter 200 also comprises an analyzing unit 414 operatively connected to the imaging unit 410 for analyzing the image data 412. The analyzing unit 414 provides matter characterization data 416 based on the collected portion of the specular reflected light beam 408 representative of the inspected matter 200. In one embodiment, the analyzing unit 414 comprises a computer unit.

The skilled addressee will appreciate that image data may comprise information for a plurality of inspection points located on the matter to inspect. Such information may comprise 2D spectral data provided by an acquisition unit such as an imaging unit.

As explained above, the analysis of specular reflected light may be of great advantage for inspection and characterization of transparent material. However, in order to provide a more convenient apparatus, it may be of great advantage that the apparatus be also well adapted for inspecting various other types of material such as opaque and/or diffusing material.

Thus, in one embodiment, the concentrated diffused lighting 406 is further adapted for generating a diffused reflected light beam representative of the inspected matter 200, as shown in FIG. 2. The skilled addressee will appreciate that the generation of the diffused reflected light beam may depend on the material of the inspected surface. Indeed, as previously explained, in the case the material under inspection is an opaque material, the top surface thereof may generate a diffused reflected light beam when enlightened with the concentrated diffused lighting 406. The imaging unit 410 is further adapted for imaging at least a portion of the diffused reflected light beam. In other words, in this embodiment, the imaging unit 410 may collect both specular and diffused reflected light. In this embodiment, the matter characterization data 416 may be further based on the collected diffused reflected light beam. This may be of great advantage since the apparatus may provide a characterization of the matter for further processing on a great variety of materials, including a continuous flow of various types of waste material, as it should become apparent to the skilled addressee upon reading the present description.

As it should be apparent from the present description, the lighting unit 404 may advantageously be adapted to maximize the specular reflections reaching the imaging unit 410.

Thus, in one embodiment, the lighting unit 404 is adapted so that specular reflections may occur for several surface angles of the object, as detailed below.

Figure 6A:
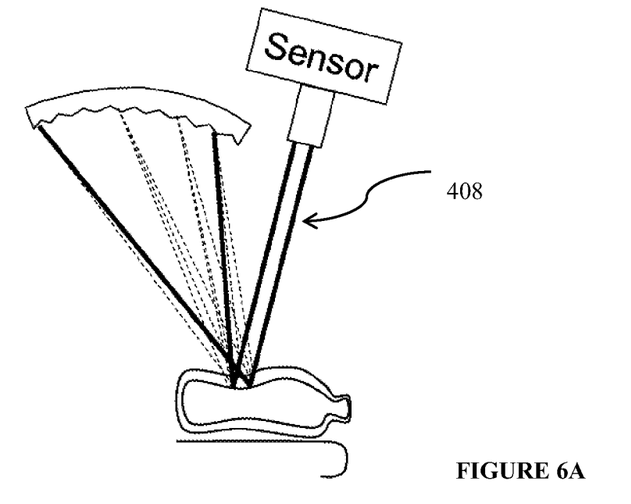
FIG. 6A shows a schematic representation of a projected concentrated diffused lighting and generated specular reflected rays reaching an imaging unit, according to one embodiment.

In a further embodiment, the concentrated diffused lighting 406 is projected angularly on the matter 402, i.e. with respect to its normal or the normal of the conveying belt, while the imaging unit 410 is positioned to maximize collection of specular reflections. The relative position may be in a facing relationship in one embodiment, with each of the lighting unit 404 and the imaging unit 410 extending at a similar angle on each side of the normal of the inspected surface as illustrated in FIG. 6A. The angle between the projected concentrated diffused lighting 406 and a normal of the object may be comprised between 0 and 60 degrees in one embodiment, although various other arrangements may be considered for a given application. For example, each of the lighting unit 404 and the imaging unit 410 may alternatively extend on a same side of a vertical normal of the inspected matter, as illustrated in FIG. 7B, for maximizing specular reflection from an obliquely oriented inspected surface, as it should become apparent below to the skilled addressee.

In one embodiment, the generated concentrated diffused lighting 406 should further be adapted so that the intensity of the collected specular reflected light beam 408 is not too high relatively to the dynamic range of the imaging element and further relatively to the intensity of the collected diffused reflected light beam. This prevents saturation issues and enables maximizing the collection of data, which may be of great advantage for inspecting matter of various materials. Moreover, it also allows the use of imaging elements whose dynamic range may be limited, such as a hyper-spectral camera for example.

To reduce intensity of the specular reflections, for a given total power, the lighting unit 404 should have an emission surface which is sufficiently great in order that the intensity in each point is sufficiently low. An increased emission surface may also improve probabilities of collection of specular reflections, which is of great advantage since it may improve measurement. In other words, the lighting unit 404 should provide a low density of lighting and a great emission surface, similarly to a fluorescent lamp for example.

To provide a low density of lighting and a great emission surface, a diffusing optical element may be used. However, in this case, a large portion of the projected lighting may be projected outside the imaged zone. In order to obtain a lighting of a sufficient density in the imaged zone, the power of the source should be increased of an order of magnitude, which may not be acceptable in most applications wherein thermic power may not be more increased.

To optimize the lighting density of the lighting unit, which may have to be limited, and also the intensity of illumination, which may have to be sufficiently high, in one embodiment, the lighting unit may be adapted to have a diffuse origin and to provide a concentrated delivery. In this case, for each measurable point in the inspection zone, there is a plurality of light rays coming from a plurality of directions.

It is also worth mentioning that the dimension of the projected concentrated diffused lighting 406 should not be too large in one embodiment, in order to limit the diffused lighting reflected by the conveying belt which may dilute the useful specular reflected light. For example, a hemispheric lighting may not be well adapted since reflected specular light and diffused light reflected by the belt may not be distinguishable from each other in some cases.

Thus, as it should become apparent to the skilled addressee, the emission surface of the light source should be large enough to provide specular reflections of a sufficiently low intensity while being small enough for providing specular reflections whose intensity is high enough without preventing the collection of the useful diffused reflections.

The skilled addressee will appreciate that such a lighting unit may be of great advantage for inspecting transparent material. Indeed, in this case, the specular reflections coming from the object may be tuned to be intense enough to cover the signal which may be reflected by the belt. The skilled addressee will also appreciate that such an embodiment may also be well adapted for inspection of diffusing objects.

Providing a sufficiently large illuminated zone as described above may be of great advantage since it may reduce misalignment issues which generally arise in the systems of the prior art wherein the illuminated zone should be carefully positioned with respect to the imaging zone. Moreover, it may also simplify manufacturing and maintenance of the apparatus, which is also of great advantage.

The apparatus may be well adapted for use in conjunction with a conveying belt. Indeed, the optimized intensity of the projected light may be sufficiently limited to prevent an undesired heating of the conveying belt, which may be of great advantage in the case the belt has to be stopped.

In one embodiment, the projected concentrated diffused lighting 406 has a solid angle comprised between 0.15 steradian and 0.6 steradian. In a further embodiment, the solid angle is 0.3 steradian, although other arrangements may be considered for a given application.

Referring again to FIG. 4, in one embodiment, the lighting unit 404 comprises a light source 418 for providing a lighting beam 420 and a converging lens 422 mounted proximal the light source 418 for concentrating the lighting beam 420 and providing a concentrated lighting 422. The lighting unit 404 also comprises a limited diffusion angle diffuser 424 mounted with the light source 418 and the converging lens 422 for diffusing the concentrated lighting 422 according to a given limited diffusion angle and thereby providing the concentrated diffused lighting 406.

In one embodiment, the converging lens 422 and the limited diffusion angle diffuser 424 may be integrated in a Fresnel lens.

In another embodiment, the light source 418 may be a white light source although other arrangements may be considered. For example, halogen lamps may be used.

Figure 5A:
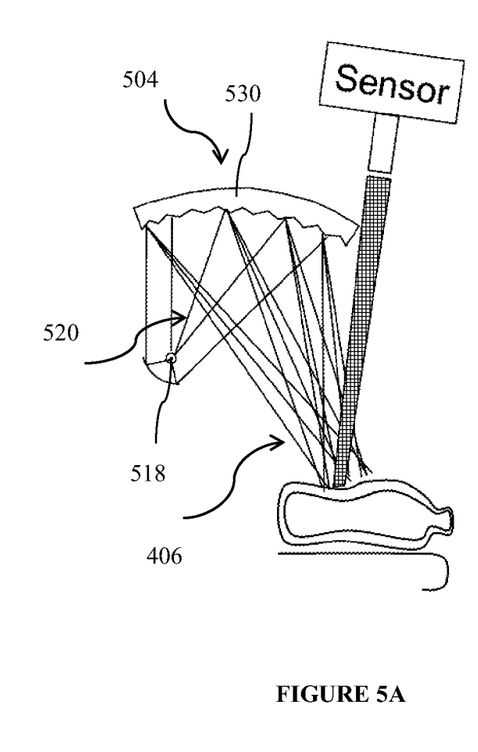
FIG. 5A shows a lighting unit of an apparatus for inspecting matter, according to another embodiment.

Referring now to FIG. 5A, in another embodiment, the lighting unit 504 comprises a light source 518 for providing a lighting beam 520 and a limited diffusion angle reflector 530 mounted with the light source 518 for reflecting the lighting beam 520 towards the matter 200 according to a given limited diffusion angle and thereby providing the concentrated diffused lighting 406.

In one embodiment, the limited diffusion angle reflector 530 comprises a patterned aluminum sheet providing a diffusing mirror. For example, a sheet of Anolux stucco MIRO®9 may be used.

Figure 5B:
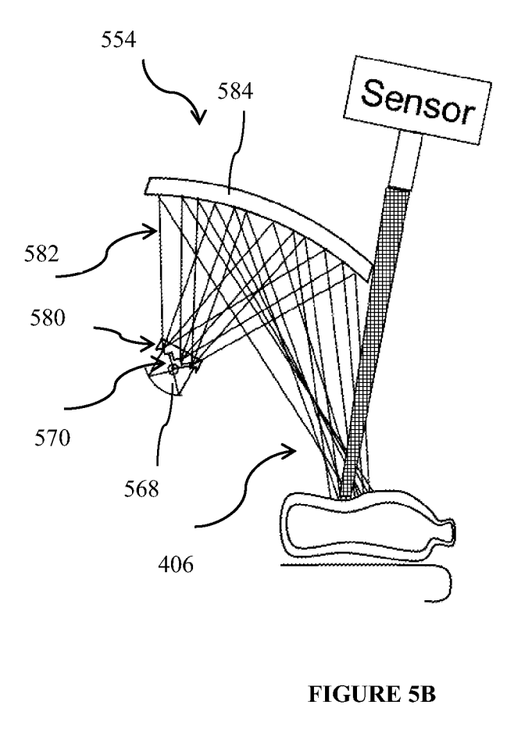
FIG. 5B shows another lighting unit of an apparatus for inspecting matter, according to still another embodiment.

Referring now to FIG. 5B, in still another embodiment, the lighting unit 554 comprises a light source 568 for providing a lighting beam 570 and a diffuser 580 mounted proximal the light source 568 for diffusing the lighting beam 570 and providing a diffused lighting 582. The lighting unit 554 also comprises a converging optical element 584 mounted with the light source 568 and the diffuser 580 for converging the diffused lighting 582 towards the matter 200 and thereby providing the concentrated diffused lighting 406.

In one embodiment, a frosted bulb is used for the light source 568 and the diffuser 580. In a further embodiment, the converging optical element 584 comprises a converging mirror but various other optical arrangements may be envisaged.

Other arrangements enabling to provide a suitable concentrated diffused lighting 406 may be considered for a given application. The skilled addressee will nevertheless appreciate that such arrangements, in one embodiment, should enable the generation of both the specular reflected light beam 408 and the diffused reflected light beam at suitable relative intensities in order to enable inspection of various material, as detailed above.

As previously explained, in one application, the apparatus 400 is used for sorting various objects of a continuous flow of matter conveyed on a conveying belt. In this case, the apparatus may be mounted above the conveying belt for projecting the concentrated diffused lighting 406 on a whole width of the conveying belt.

As mentioned above, the given imaging angle may be chosen to specifically maximize or minimize the specular reflected light coming from horizontal surfaces or other specifically oriented surfaces.

FIG. 7A shows an embodiment which is particularly well adapted for maximizing specular reflections of horizontal surfaces and substantially horizontal surfaces. In this embodiment, as illustrated, the projected concentrated diffused lighting 406 and the imaging unit 410 extend at a similar angle on each side of a normal of the matter. In the illustrated embodiment, the similar angle is 5 degrees.

As it should become apparent to the skilled addressee, this embodiment is of great advantage. Indeed, it enables to maximize the surfaces which may be imaged since substantially horizontal surfaces statistically appear more frequently in some applications. Moreover, it may enable to keep most of the collected image data in a given dynamic range, which is also of great advantage.

FIG. 7B shows an embodiment of another configuration which is particularly well adapted for limiting specular reflections of horizontal surfaces. In this embodiment, as illustrated, the projected concentrated diffused lighting 406 and the imaging unit 410 extend on the same side of the normal of the matter. In the illustrated embodiment, the imaging unit 410 extends at 10 degrees. Such a configuration may be of great interest for maximizing specular reflections coming from surfaces whose normal extends at equidistance between the imaging unit 410 and the lighting unit 404.

As it should become apparent to the skilled addressee, this embodiment may be of great advantage since it may enable to enhance detection of extremities of given elements such as plastic bottles as a non-limitative example.

Moreover, light reflected from the conveying belt may also be limited. This may be of great advantage for given applications, for example for limiting the portion of the reflected light coming from a clean or smooth conveying belt and which may not be reliable in some conditions.

FIG. 8A shows experimental image data obtained with the configuration of FIG. 7A while FIG. 8B shows experimental image data obtained with the configuration of FIG. 7B. The skilled addressee will appreciate that both configurations provide suitable image data for a crushed transparent bottle 802 and an uncrushed transparent bottle 804. The skilled addressee will nevertheless appreciate that an object 806 with flat horizontal surfaces may not be conveniently detected in specific conditions with the configuration of FIG. 7B, as detailed below.

Indeed, the left half of both FIGS. 8A and 8B shows a clean conveying belt 808 while the right half shows a dirty conveying belt. As illustrated, in the configuration of FIG. 7A (see FIG. 8A), the image data comprise reflected light coming from the conveying belt for both a clean and a dirty conveying belt. In the configuration of FIG. 7B (see FIG. 8B), the image data comprise much less information coming from the belt when the belt in clean. As previously explained, this may be of great advantage for enhancing detection of non-horizontal surfaces of objects. However, detection of flat objects may be more difficult, as illustrated.

Experimental results have shown that for (a) a light uncrushed object on a clean belt, (b) a light crushed object on a clean belt, (c) a light flat object on a clean belt, (d) a clean belt alone, (e) an object on a dirty and dry belt and (f) an object on a dirty and wet belt, characterization of the material is greatly enhanced with the configuration of FIG. 7A compared to the systems of the prior art. These results also show that the configuration of FIG. 7B may also provide an enhanced detection for (a), (b), (e) and (f) compared to the systems of the prior art.

In order to provide a more versatile apparatus, in one embodiment, an additional lighting unit mounted according to a given mounting angle with respect to the lighting unit may be used to generate an additional specular reflected light beam. In one embodiment, each of the lighting units may be mounted at different angles in order to maximize specular reflections coming from various angles, as it should become apparent to the skilled addressee. This may be of great advantage for maximizing both the specular reflected lighting coming from the horizontal surfaces and the specular reflected lighting coming from the extremities of the inspected objects.

Figure 6B:
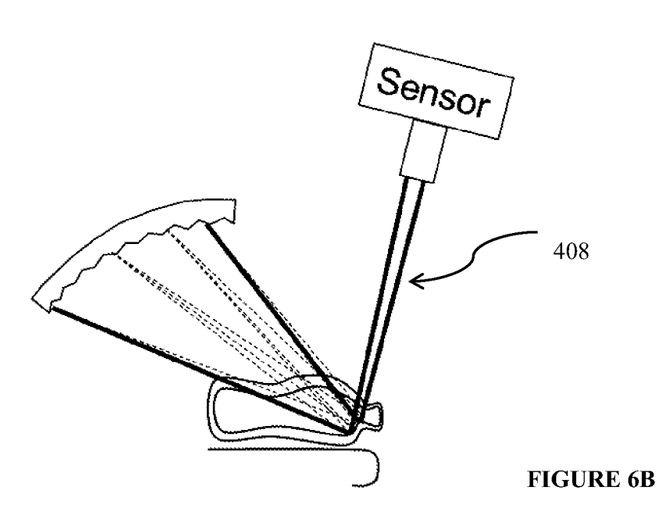
FIG. 6B shows another schematic representation of a projected concentrated diffused lighting and generated specular reflected rays reaching an imaging unit, according to another embodiment.

For example, each of the lighting units may be mounted according to the angular configurations shown in FIGS. 6A and 6B respectively while the imaging unit is mounted to collect reflected light coming from both lighting units. This embodiment may be of great advantage to enable detection of horizontal surfaces as well as detection of extremities of given elements such as plastic bottles as a non-limitative example.

In still a further embodiment, the apparatus may be provided with a control unit (not shown) operatively connected to the lighting unit for controlling projection of the concentrated diffused lighting and thereby relative intensities of the specular reflected light beam and the diffused reflected light beam.

In one embodiment, the solid angle of the projected concentrated diffused lighting 406 may be adjusted according to a given application. This may be of great advantage in the case the apparatus is used with various types of material. Indeed, in this case, the solid angle of the projected concentrated diffused lighting 406 may be adjusted so that the intensity of the specular reflected light beam and the intensity of the diffused reflected light beam extend in a similar useful range with respect to the imaging unit 410.

As it should become apparent to the skilled addressee, in one embodiment, the matter characterization data may be used for sorting different types of material such as plastic, metallic or cardboard objects.

In a further embodiment, the characterization of material may comprise identification thereof. In other words, the spectral absorption of the material which may be determined may be used to identify specific types of plastic material. This may be of great advantage for automatically sorting and classifying recyclable plastic objects in a recycling center, as it should become apparent to the skilled addressee.

Figure 9:
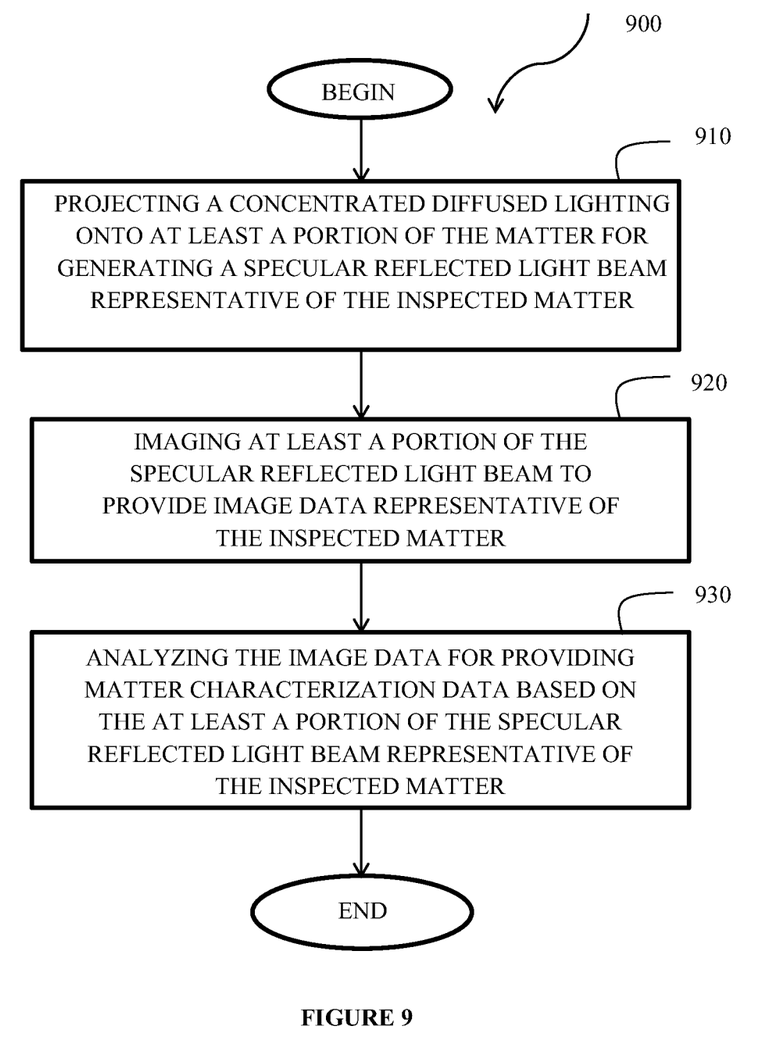
FIG. 9 is a flow chart of a method for inspecting matter, in accordance with one embodiment.

Referring to FIG. 9, a method 900 for automatically inspecting matter will now be described.

According to processing step 910, a concentrated diffused lighting is projected onto at least a portion of the matter for generating a specular reflected light beam representative of the inspected matter. As previously mentioned, in the illustrated embodiment, the concentrated diffused lighting is angularly projected onto the inspected matter but other arrangements may be considered for a given application.

According to processing step 920, at least a portion of the specular reflected light beam is imaged or collected to provide image data representative of the inspected matter.

According to processing step 930, the image data are analysed for providing matter characterization data based on the at least a portion of the specular reflected light beam representative of the inspected matter.

In one embodiment, as mentioned above, a diffused reflected light beam may also be used in addition to the specular reflected beam in order to image various types of materials including diffusing materials. Thus, in this embodiment, the processing step of projecting the concentrated diffused lighting is further adapted to further generate a diffused reflected light beam representative of the inspected matter, as described above. The method further comprises processing step of imaging at least a portion of the diffused reflected light beam. In this embodiment, the processing step of analyzing the image data is further based on the collected diffused reflected light beam.

In one embodiment, processing step of projecting and processing step of imaging are performed at a similar angle on each side of a normal of the matter, as previously explained.

In another embodiment, processing step of projecting and processing step of imaging are performed on a side of a vertical normal of the matter, as previously explained.

In one embodiment, as illustrated in FIG. 4, processing step of projecting a concentrated diffused lighting 406 onto the matter 200 comprises providing a lighting beam 420; concentrating the lighting beam 420 to provide a concentrated lighting 422; and diffusing the concentrated lighting 422 according to a given limited diffusion angle to thereby provide the concentrated diffused lighting 406.

In an alternative embodiment, as illustrated in FIG. 5A, processing step of projecting a concentrated diffused lighting 406 comprises providing a lighting beam 520; and reflecting the lighting beam 520 towards the matter 200 according to a given limited diffusion angle to thereby provide the concentrated diffused lighting 406.

In another embodiment, as illustrated in FIG. 5B, processing step of projecting a concentrated diffused lighting 406 comprises providing a lighting beam 570; diffusing the lighting beam 570 for providing a diffused lighting 582; and converging the diffused lighting 582 towards the matter 200 to thereby provide the concentrated diffused lighting 406.

Throughout the present description, the apparatus and the method have been mainly described in the context of material sorting and classification applications. It is nevertheless worth to mention that various other applications may be envisaged. For example, the apparatus and the method may be used to provide inspection data based on the matter characterization data to enable a defect inspection of the matter, as it should become apparent to the skilled addressee. One application may be the control of a continuous process manufacturing laminated sheet of Plexiglas for example.

The skilled addressee will appreciate that the described apparatus may be of great advantage in given environments such as dirty environments wherein the use of configurations with each of the imaging unit and the lighting unit extending on each side of the matter respectively may be prevented.

Although the above description relates to specific preferred embodiments as presently contemplated by the inventor, it will be understood that the invention in its broad aspect is not limited to this specific embodiment and includes mechanical and functional equivalents of the elements described herein.

What is claimed is:

1. An apparatus for inspecting recyclable matter, said apparatus comprising:
   a lighting unit for projecting a concentrated diffused lighting onto at least a portion of said recyclable matter to generate a specular reflected light beam representative of the inspected recyclable matter;
   an imaging unit mounted according to a given imaging angle with respect to the projected concentrated diffused lighting for imaging at least a portion of the specular reflected light beam to provide spectral data representative of the inspected recyclable matter;
   an analyzing unit operatively connected to the imaging unit for analyzing the spectral data and providing recyclable matter characterization data based on the at least a portion of the specular reflected light beam representative of the inspected recyclable matter; and wherein the specular reflected light beam comprises specular rays selected from a group consisting of specular rays of second surface, specular ray of third surface, specular rays of fourth surface and specular rays of a supporting surface supporting said recyclable matter.

2. The apparatus for inspecting recyclable matter according to claim 1, wherein the concentrated diffused lighting is angularly projected onto the at least a portion of said recyclable matter.

3. The apparatus for inspecting recyclable matter according to claim 1, wherein the concentrated diffused lighting further generates a diffused reflected light beam representative of the inspected recyclable matter.

4. The apparatus for inspecting recyclable matter according to claim 3, wherein the imaging unit is adapted for imaging at least a portion of the diffused reflected light beam and wherein the recyclable matter characterization data are further based on the at least a portion of the diffused reflected light beam.

5. The apparatus for inspecting recyclable matter according to claim 1, wherein the projected concentrated diffused lighting has a solid angle comprised between 0.15 steradian and 0.6 steradian.

6. The apparatus for inspecting recyclable matter according to claim 1, wherein the projected concentrated diffused lighting and the imaging unit extend one of at a similar angle on each side of a normal of a supporting surface supporting the recyclable matter and on a side of a normal of a supporting surface supporting said recyclable matter.

7. The apparatus for inspecting recyclable matter according to claim 1, wherein the lighting unit comprises a converging lens and a limited diffusion angle diffuser mounted with a light source, the converging lens being mounted proximal the light source.

8. The apparatus for inspecting recyclable matter according to claim 1, wherein the lighting unit comprises a limited diffusion angle reflector mounted with a light source, wherein the limited diffusion angle reflector comprises an aluminum sheet providing a diffusing mirror.

9. The apparatus for inspecting recyclable matter according to claim 1, wherein the lighting unit comprises a diffuser and a converging optical element mounted with a light source, the diffuser being mounted proximal the light source.

10. The apparatus for inspecting recyclable matter according to claim 1, further comprising at least one additional lighting unit mounted according to a given mounting angle with respect to the lighting unit to generate an additional specular reflected light beam.

11. The apparatus for inspecting recyclable matter according to claim 1, wherein said recyclable matter comprises at least one of transparent material and waste of differing materials.

12. The apparatus for inspecting recyclable matter according to claim 1, wherein the recyclable matter characterization data comprises at least one of recyclable matter identification data and inspecting data enabling defect inspection of the recyclable matter.

13. A method for automatically inspecting recyclable matter, said method comprising:
projecting a concentrated diffused lighting onto at least a portion of said recyclable matter for generating a specular reflected light beam representative of the inspected recyclable matter;
imaging at least a portion of the specular reflected light beam to provide spectral data representative of the inspected recyclable matter; and
analyzing the spectral data for providing recyclable matter characterization data based on the at least a portion of the specular reflected light beam representative of the inspected recyclable matter; wherein the specular reflected light beam comprises a plurality of specular rays selected from a group consisting of specular rays of second surface (204), specular rays of third surface (302) and specular rays of fourth surface (206) of said inspected recyclable matter and/or comprises specular rays (212) of a supporting surface (210) supporting said recyclable matter.

14. The method for inspecting recyclable matter according to claim 13, wherein imaging comprises imaging specular rays of a supporting surface supporting said recyclable matter.

15. The method for inspecting recyclable matter according to claim 13, wherein projecting the concentrated diffused lighting further generates a diffused reflected light beam representative of the inspected recyclable matter.

16. The method for inspecting recyclable matter according to claim 15, further comprising imaging at least a portion of the diffused reflected light beam, and wherein analyzing the spectral data is further based on the at least a portion of the diffused reflected light beam.

17. The method for inspecting recyclable matter according to claim 13, wherein projecting and imaging are performed one of at a similar angle on each side of a normal of the recyclable matter and on a side of a normal of a supporting surface supporting said recyclable matter.

18. The method for inspecting matter according to claim 13, wherein projecting a concentrated diffused lighting onto at least a portion of said recyclable matter comprises:
providing a lighting beam;
and one of
A. concentrating the lighting beam to provide a concentrated lighting and diffusing the concentrated lighting according to a given limited diffusion angle to thereby provide the concentrated diffused lighting;
B. reflecting the lighting beam towards the at least a portion of said recyclable matter according to a given limited diffusion angle to thereby provide the concentrated diffused lighting; and
C. diffusing the lighting beam for providing a diffused lighting and converging the diffused lighting towards the at least a portion of said recyclable matter to thereby provide the concentrated diffused lighting.

19. The method for inspecting recyclable matter according to claim 13, further comprising:
projecting an additional concentrated diffused lighting onto the at least a portion of said recyclable matter for generating an additional specular reflected light beam representative of the inspected recyclable matter; and
imaging at least a portion of the additional reflected light beam to provide additional spectral data representative of the inspected recyclable matter.

20. The method for inspecting recyclable matter according to claim 13, wherein analyzing the spectral data comprises determining a spectral absorption of the inspected recyclable matter.

21. Use of the method for inspecting recyclable matter as defined in claim 13 for one of automatic material sorting, automatic classification of transparent material, automatic manufacturing process control and automatic inspection of a continuous flow of recyclable matter.

* * * * *